United States Patent [19]  
Freal-Saison

[11] Patent Number: 4,874,498
[45] Date of Patent: Oct. 17, 1989

[54] APPARATUS FOR REGULATING THE CONCENTRATION OF AN OXIDIZING SOLUTION BY MEASURING THE REDOX POTENTIAL THEREOF

[75] Inventor: Jean-Michel Freal-Saison, Chatou, France

[73] Assignee: Henkel France S.A., Gentilly, France

[21] Appl. No.: 25,958

[22] Filed: Mar. 16, 1987

[30] Foreign Application Priority Data

Mar. 17, 1986 [FR] France .................. 86 03745

[51] Int. Cl.⁴ ............ G01N 27/26; G01N 27/28
[52] U.S. Cl. .................. 204/400; 204/1 T; 204/409; 204/433
[58] Field of Search ........... 204/400, 409, 443, 1 T; 324/438, 439, 450

[56] References Cited

U.S. PATENT DOCUMENTS

| 2,607,718 | 6/1946 | Suthard | 204/400 |
| 2,782,151 | 2/1957 | Suthard | 324/438 |
| 3,950,137 | 4/1976 | Larson | 324/439 |
| 4,151,255 | 4/1979 | Capuano | 204/433 |
| 4,315,518 | 2/1982 | Sawyer | 204/433 |
| 4,477,329 | 10/1984 | Rogers | 204/1 T |
| 4,533,440 | 8/1985 | Kim | 204/400 |
| 4,609,870 | 9/1986 | Reich | 204/409 |

OTHER PUBLICATIONS

A. L. Cuartero, "Automotic Chloration of Swimming Pool Water by Measuring and Regulation of the Redox Potential", Review L'eau l'industrie, les nuisances, No. 75, p. 54, Jun./Jul. 1983.

Primary Examiner—John F. Niebling
Assistant Examiner—Ben C. Hsing
Attorney, Agent, or Firm—Hughes & Multer

[57] ABSTRACT (a) Apparatus for regulating the concentration of an oxidizing solution, particularly a solution containing disinfecting molecules.

(b) Apparatus characterized in that it comprises a secondary pipe (6) branched to a main pipe (1) upstream of a readjustment pipe (5) to which is fitted a measuring cell (2), as well as an addition pipe (12) connected to a reservoir (8) containing an adapting solution (7).

21 Claims, 4 Drawing Sheets

APPARATUS FOR REGULATING THE CONCENTRATION OF AN OXIDIZING SOLUTION BY MEASURING THE REDOX POTENTIAL THEREOF

The present invention relates to an apparatus for regulating the concentration of an oxidizing solution, particularly a solution containing disinfecting molecules used on an industrial scale and flowing in closed circuit manner in a main pipe, more particularly forming part of a cleaning and/or disinfecting installation by measuring the redox potential of said solution.

The invention can be more particularly used in a cleaning system with recovery of the solution, such as is described in French Pat. No. 85 03 935, or in a cleaning system without any recovery of the solution, but which has a closed circuit for the preparation of the latter.

In the food industry and more particularly the dairy industry, following the standard cleaning and rinsing operations, it is necessary to circulate an oxidizing disinfecting solution which can contain peracetic acid and/or hydrogen peroxide. However, to satisfy the hygiene rules, it is vital that said disinfecting operation makes it possible to at least destroy all the pathogenic or troublesome microorganisms.

To obtain this result, it is necessary to check that the concentration of disinfecting molecules in the oxidizing disinfecting solution does not drop below a minimum predetermined value.

The simplest way of achieving this is to carry out manual titrations at predetermined time intervals. However, such titrations take a long time and therefore involve high manpower costs. Therefore attempts have been made to replace these manual methods by automatic methods.

Among the hitherto proposed methods, reference is made to the use of known automatic analyzers, such as those sold under the "INTEROX" or "HARSHAW" marks. These apparatuses permit a complete dosing or metering of the oxidizing molecules of the concentration, but cannot be industrially used as a result of their excessive purchase price, their complicated maintenance and their excessive response time.

To obviate these disadvantages, French Pat. No. 85 03 935 proposes a process for regulating the concentration of disinfecting solutions in which, by using a measuring probe placed in the disinfecting solution, measurement takes place of the value of a measuring parameter dependent on the concentration of disinfecting molecules. The measured value is compared with a desired value and if the measured real value differs from the desired value, a dosing pump is started up or an electrovalve associated with a reservoir containing a concentrated solution of disinfecting molecules is opened, so as to inject into the disinfecting solution, disinfecting molecules in adequate quantities to reestablish the desired value of the concentration, said injection being automatically stopped when the desired value is reached.

The envisaged measuring parameters include the conductivity of the disinfecting solution, its pH, or even its colour following a colorimetric or characteristic chemical reaction. These parameters have the advantages and disadvantages inherent therein.

Another parameter which can be used is the redox potential. Unfortunately, as can be gathered from the curve in FIG. 7, which shows the variations of the potential (mv) of a solution as a function of its concentration of peroxidized chemical products, the redox potential is only directly related to the concentration for low disinfecting molecule concentrations and for constant pH-values. Moreover, when the disinfecting molecule concentration rises, the slope of the curve rH=f(c) decreases very rapidly, until said curve becomes substantially flat and therefore unusable.

Thus, for random concentrations, the redox potential of a solution is dependent on its pH, in accordance with the formula:

$$E = Eo + \frac{RT}{nF} \text{Ln} \frac{(Ox)}{(Red)}$$

in which:
Eo=normal equilibrium potential,
R=constant of perfect gases,
T=absolute temperature,
F=Faraday constant,
n=number of electrons involved.

In the case of peroxides (n=2) and for a temperature of 18° C., this relation becomes:
E=0.029 rH−0.058 pH (rH being the redox potential).

Consequently and as has been stated in French Pat. No. 85 03 935, if it is wished to use the redox potential of the disinfecting solution as a measuring parameter, it is either necessary to previously dilute the latter, or to take account of the pH of the solution, or to maintain the pH constant by adding a buffer element to the disinfecting solution.

However, hitherto no apparatus has been proposed enabling the carrying out in a simple manner of one of these measurements directly on the circulating solution.

The present invention aims at filling this gap by proposing an apparatus for regulating the concentration of an oxidizing solution, particularly a solution containing disinfecting molecules used on an industrial scale and circulating in closed circuit manner in a main pipe more particularly belonging to the type of installation called a "in situ cleaning station", or to an installation for the closed circuit preparation of a disinfecting solution incorporating a preparation tank, by measuring the redox potential of said solution, said installation having a readjustment pump, as well as a measuring cell with an electrode for measuring the redox potential of the oxidizing solution and an electrode for measuring the pH of said solution, associated with a regulator able to determine the real value for disinfecting molecules on the basis of signals transmitted by the probe, compare said real value with a desired value and, if the real value differs from the desired value, to control the putting into operation of the readjustment pump or the electrovalve, so as to inject an adequate quantity of disinfecting molecules into the main pipe to reestablish the desired value of the concentration, said injection being automatically stopped when the desired value is reached, whereby said installation also has a reservoir of a concentrated solution of disinfecting molecules connected to the main pipe by a readjustment pipe.

According to the invention, this apparatus is characterized in that it comprises a secondary pipe branched on the main pipe upstream of the readjustment pipe in the closed circuit flow direction of the disinfecting solution and on which is mounted, particularly branched, the measuring cell, together with an addition pipe connected on the one hand to the secondary pipe or to an auxiliary pipe branched to the latter upstream of the measuring electrodes in the disinfecting solution flow direction and on the other hand to a reservoir containing an adapting solution which can be added in a given proportion to the disinfecting solution in order to reduce its redox potential to a level making it possible to measure and buffer the pH of the medium, the secondary pipe as well as the addition pipe, and, if appropriate, the auxiliary pipe, being equipped with circulating members, particularly pumps, making it possible to circulate the disinfecting solution and the adapting solution.

Thus, the apparatus according to the invention makes it possible to displace the measuring point on the redox potential/concentration curve into an area where the variation is fast, prevent the polarization of the measuring electrode and, simultaneously, operate at a constant pH (i.e. always on the same curve in accordance with the diagram appearing in the appendix).

The essential advantage of this apparatus is that it makes it possible to follow and continuously readjust the disinfectant concentration. After measurement, the solution in the secondary pipe is led directly to the drain.

According to another feature of the invention, the apparatus is equipped with safety devices able to detect an operating abnormality, particularly the failure of a pump, the absence of adapting solution in the measuring cell, etc. and to trigger an alarm in response thereto.

This equipment is also provided in certain cases with means for detecting the breaking of circulating pipes.

According to another feature of the invention, the regulator has at least one set point associated with the measurement of the pH and preferably has two set points, namely a high set point and a low set point.

Among the regulators which can be used according to the invention are the means marketed under the trade mark Dulcometer available under the references RHWS 1000 F1 K2; PHWS 014 F1 K2; PRW2 F1 K2.

According to this configuration, the regulator consequently simultaneously receives the signals from the electrode for measuring the redox potential of the oxidizing solution used for effecting the actual regulation and the signals from the pH measuring electrode, which in reality have a safety function.

Thus, if the pH reaches or exceeds the high set point, which means that there is no disinfecting solution or an abnormal disinfecting solution concentration to the right of the measuring electrodes. However, if the pH reaches or exceeds the low set point, this means an absence of adapting reagent or an abnormal excessive concentration of the solution. In both cases, the regulator triggers an alarm and stops the installation.

According to the invention, the secondary pipe cannot be continuously supplied, but has instead an electrovalve mounted directly downstream of the main pipe or following a manual isolating valve and supplies the measuring electrodes when regulation is possible.

As indicated hereinbefore, the function of the adapting solution is to depolarize the redox potential measuring electrode, move same into a larger variation zone for increasing the precision of the regulation and maintain the pH constant at the time of the measurement.

To this end and according to another feature of the invention, the adapting solution contains between 0 and 50% by weight of a reducing agent, between 0 and 50% by weight of an alkali compound, particularly ammonia, and between 0 and 50% by weight of a buffer element, particularly a salt, e.g. an alkali metal salt or ammonium acetate and, if appropriate, said solution is completed or topped up with demineralized water.

According to the invention, the reducing agent can be chosen from among conventional reducing agents, e.g. alkali metal thiosulphates, bisulphites, sulphites or hypophosphites, as well as organic reducing agents such as hydrazines. In actual fact the buffer salts used are similar to the solutions used in a conventional manner for calibrating pH-meters.

Obviously the characteristics of the adapting solution must in particular be adapted to the concentration of the solutions to be regulated. Thus, the disinfectant can contain a varying acid quantity, as a function of the industrial operations for which it is to be used, so that a buffer of varying strength is required for stabilizing its pH.

The adapting solution is mixed with the solution to be regulated in a flow ratio varying with the concentration of the disinfecting solution, so as to in general obtain a pH between 5 and 10. It can approximately range from one volume of disinfecting solution for one volume of adapting solution to one volume of adapting solution for five hundred volumes of disinfecting solution.

According to another feature of the invention, an adapting solution which has proved particularly advantageous is approximately formed from 2.5% by weight of ammonia, 25% by weight of ammonium acetate, 12.5% by weight of sodium bisulphite and 60% by weight of demineralized water.

According to another feature of the invention the apparatus incorporates a measuring device constituting a unitary assembly having on the one hand the circulating pumps and on the other a measuring cell with a reaction chamber in which the adapting solution is added to the disinfecting solution and mixed therewith, as well as a measuring chamber containing the two measuring electrodes and into which is introduced the solution following mixing.

The features of the apparatus according to the invention will be described in greater detail hereinafter with reference to the attached drawings, wherein show:

FIG. 1 A basic diagram of the apparatus.

FIG. 2 A longitudinal sectional view of the measuring cell.

FIG. 3 A elevational view of the cover of said cell.

Figures 4, 4A:
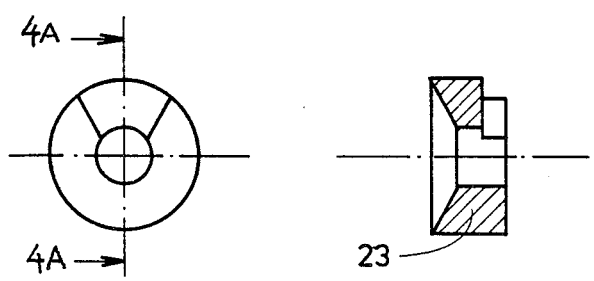
FIG. 4 is an elevational view of a piston equipping the reaction chamber.

FIG. 4A A sectional view of a piston equipping the reaction chamber.

Figure 2:
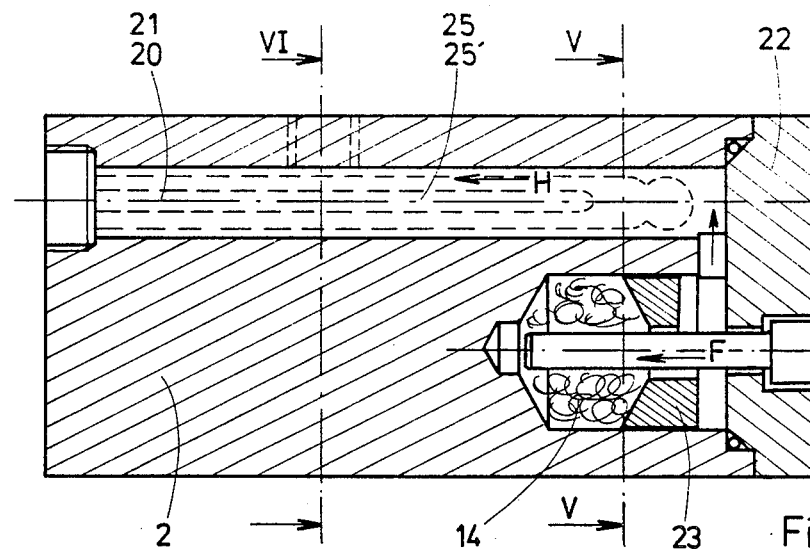
Figures 3, 3A:
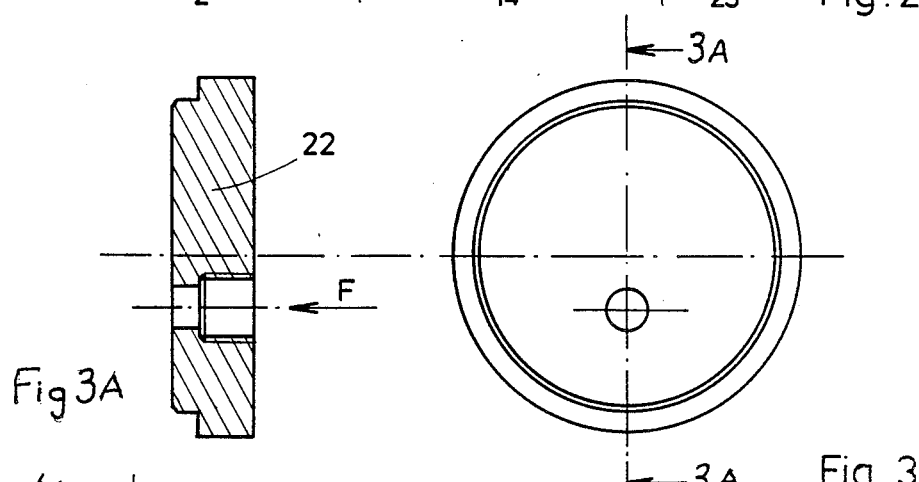
FIG. 3A is a sectional view taken along line 3A—3A of FIG. 3.
Figure 5:
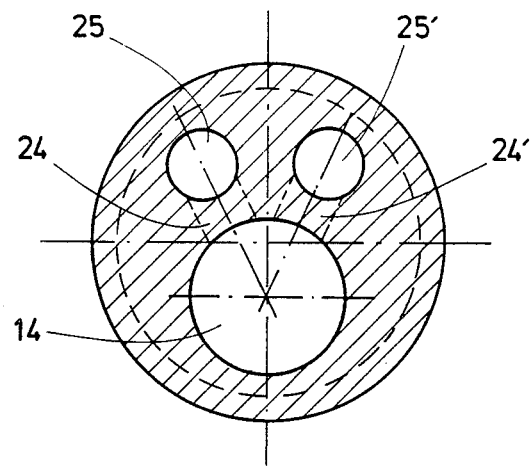

FIG. 5 A section along axis V—V of FIG. 2.

Figure 6:
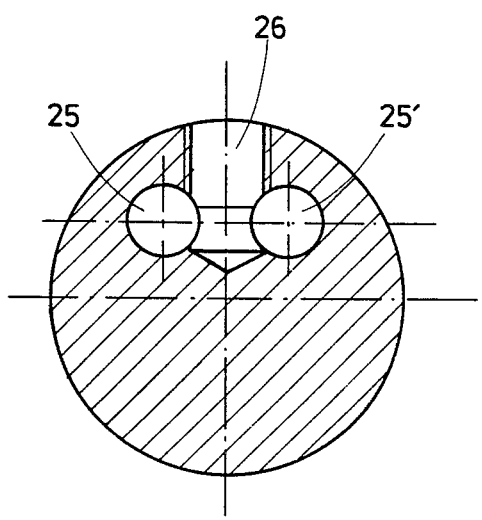

FIG. 6 A section along axis VI—VI of FIG. 2.

Figure 7:
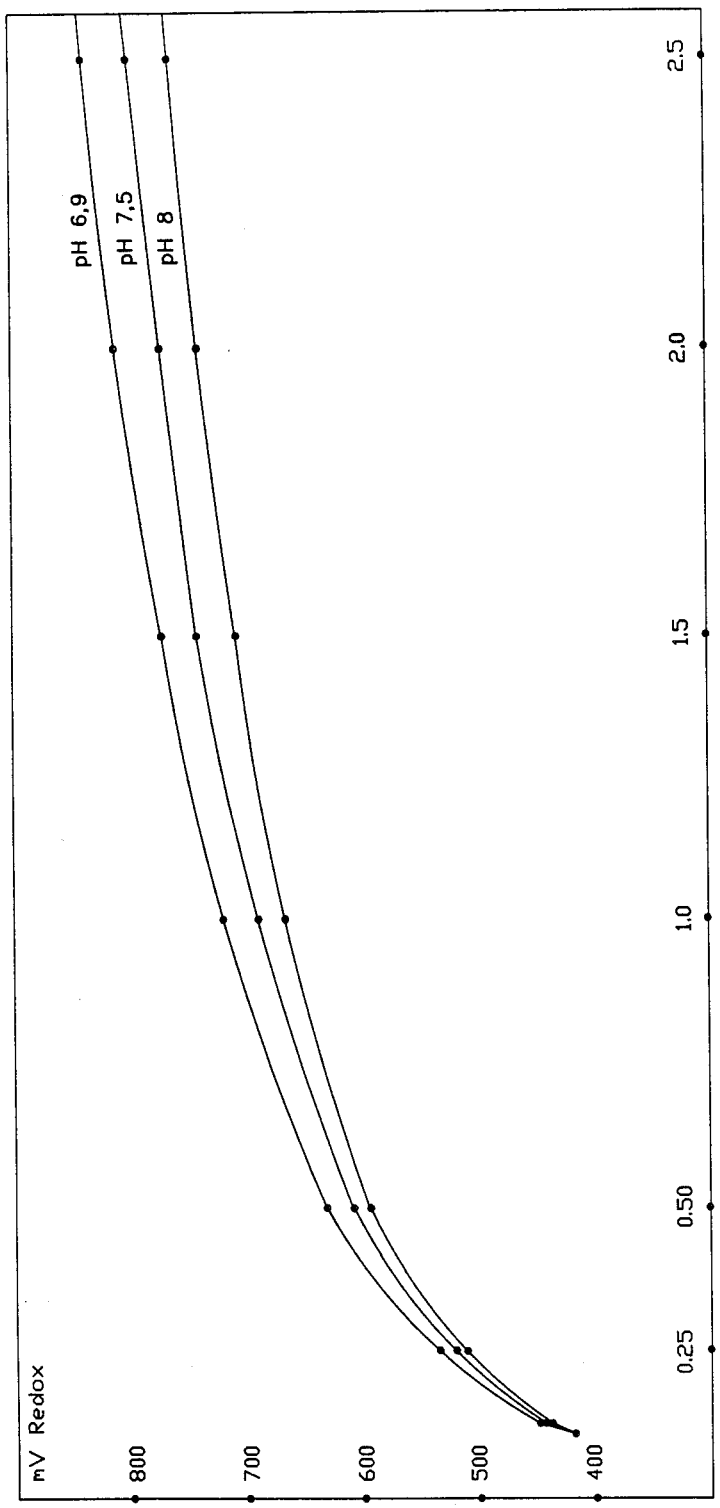

FIG. 7 is a graph which shows curves of Redox Potential variation of a solution of oxidized water depending on the concentration of the solution.

Figure 1:
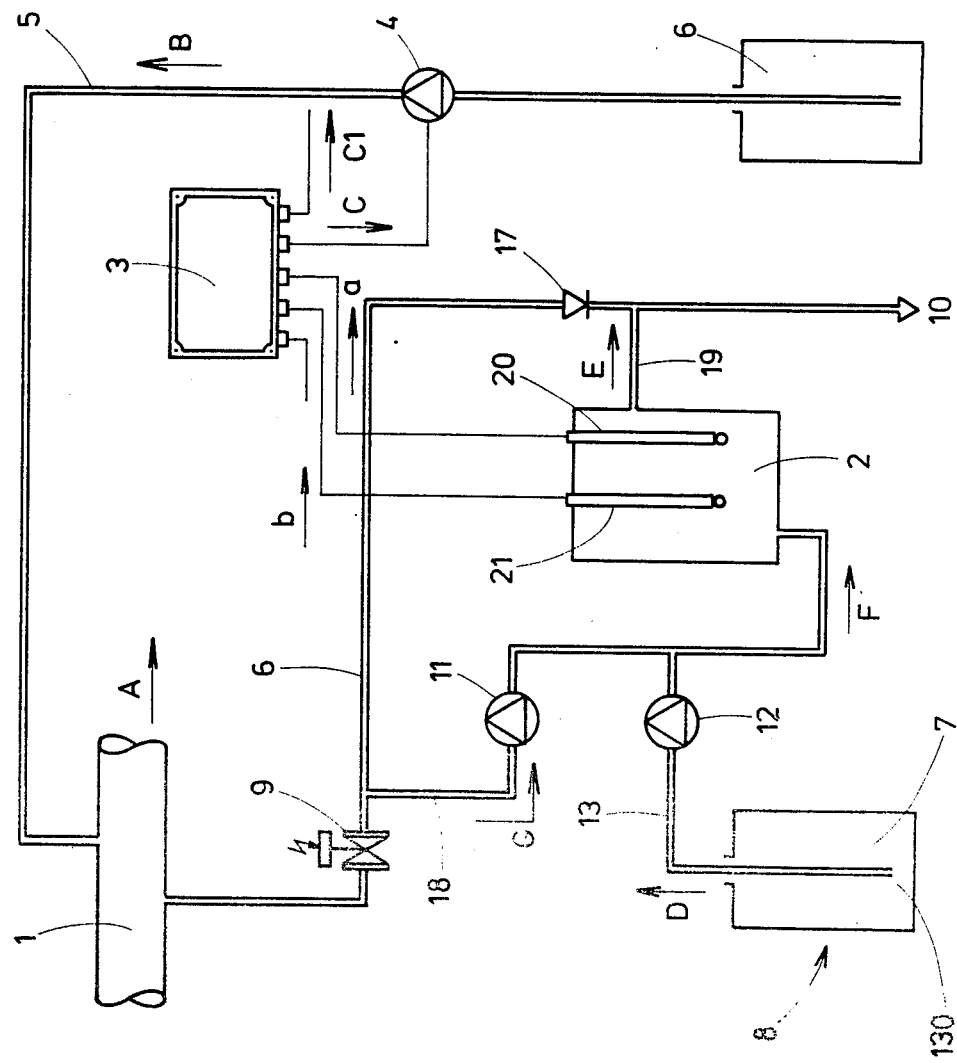

According to FIG. 1, the apparatus according to the invention is used for regulating the concentration of disinfecting molecules in an oxidizing solution circulating in closed circuit form in a main pipe 1 forming part of a so-called "in situ cleaning station" or "short circuit" of a solution preparation tank in the direction indicated by arrow A. This regulation takes place in a measuring cell 2 having a redox potential measuring electrode 20 and a solution pH measuring electrode 21.

Electrodes 20, 21 are associated with a regulator 3 which, in the direction of arrows a and b, receives signals transmitted by electrodes 20, 21 and on return measures the redox potential directly related with the real disinfecting molecule concentration of the solution circulating in closed circuit form in pipe 1, in accordance with the aforementioned formula $E = 0.029 \text{ rH} - 0.058 \text{ pH}$.

In parallel with this measurement, regulator 3 compares the real disinfecting molecule concentration with a desired value and, in the case that the desired value differs from the real value, which means that the disinfecting molecule concentration of the solution circulating in the main pipe 1 is inadequate, it transmits in the direction of arrow c a signal controlling the putting into operation of a readjustment pump 4 connected to a readjustment pipe 5, which is on the one hand connected to the main pipe 1 and on the other to a reservoir 6 containing a concentrated solution of disinfecting molecules. Thus, a signal c transmitted by regulator 3 to readjustment pump 4 automatically controls the delivery, in accordance with arrow B, of a concentrated solution of disinfecting molecules into readjustment pipe 5 until the desired concentration value is obtained in the "in situ cleaning station" to which the main pipe 1 belongs.

As stated hereinbefore, regulator 3 has a low set point and a high set point associated with the measurement of the pH. When the signal b transmitted by the pH measuring electrode 21 does not correspond to a pH between the high set point and the low set point, regulator 3 emits an alarm signal c1 which stops the apparatus.

To make it possible to link under optimum conditions the measurement of the redox potential of the oxidizing solution and the real concentration of disinfecting molecules in said solution, it is useful not only to maintain a constant pH (i.e. to be on a single pH curve), but also to be within an area indicated by the letter X on the curves $\text{rH} = f(c)$ in the appendix, so as to have a rapid variation of the potential as a function of the concentration (highly sloping zone) and avoid the polarization of the redox potential measuring electrode 20.

For this purpose, during the operation of the regulator, a predetermined proportion, chosen as a function of the concentration of the disinfecting product in an adapting solution 7 originally contained in a reservoir 8 is continuously added to cell 2.

To permit this additon and the performance of different measurements, there is a secondary pipe 6 branched to the main pipe 1 upstream of the readjustment pipe 5 in the disinfecting solution flow direction A. This pipe makes it possible to tap off part of the cleaning liquid circulating in the "in situ cleaning station" so as to pass it to the measuring cell 2. Pipe 6, which has an electrovalve 9 fitted directly or downstream of a not shown manual isolating valve downstream of the main pipe 1 is connected to the drain 10 by means of a calibrated valve 17 whose function, as will be shown hereinafter, is to protect electrodes 20, 21 by preventing any overpressure in cell 2, which is mounted on an auxiliary pipe 18 branched to the secondary pipe 6.

In order to permit the introduction to the right of electrodes 20, 21 of measuring cell 2 of a predetermined proportion of the adapting solution 7 in reservoir 8 added to the disinfecting solution, an addition pipe 13 is provided, which is connected to the axuiliary pipe 18 upstream of the measuring cell 2, whereof end 130 is immersed in reservoir 8 containing adapting solution 7.

The circulation in the direction of arrow G of the disinfecting solution in auxiliary pipe 18 and the circulation in accordance with arrow D of adapting solution 7 in addition pipe 13 are respectively controlled by circulating pumps 11, 12 positioned upstream of cell 2. Pump 11 could also be positioned downstream of said cell without passing beyond the scope of the invention.

On leaving cell 2, the mixture of the solutions from pipes 18 and 13 is directly transferred to drain 10 (arrow E) by a discharge pipe 19.

Apart from the various components referred to hereinbefore, the apparatus could also incorporate other not shown members which are sensitive to a random failure or fault of the apparatus and which can trigger an alarm to stop it.

Moreover, the aforementioned apparatus could also, according to the invention, be adapted by carrying out not shown minor modifications, so as to make it possible to carry out sorting or selecting operations between the disinfecting solution and the rinsing water. In order to adapt to such a procedure, it would be necessary to reduce the distance between the sampling of the solution circulating in the main pipe 1 and the measuring points (electrodes 20 and 21). To this end, it would be necessary to replace pump 11 of the apparatus positioned upstream of the measuring cell 2 by a pump positioned downstream (which would amount to sucking the disinfecting solution in instead of forcing it out).

According to FIGS. 2 to 6 the mixture of the disinfecting solution and the adapting solution of auxiliary pipe 18 enters, in accordance with arrow F, into the measuring cell 2, which is equipped with a cover 22. The mixture to be dosed then enters a reaction chamber 14, whose volume can be modified by means of piston 23 shown in FIG. 4. In chamber 14, the liquid to be measured is subject to vigorous whirling, which entrains its mixture with chemical reaction. This mixing can be improved by the presence of a lining of the Raschig ring type. In a second stage and as can more particularly be seen in FIG. 5, the liquid returns rearwards in accordance with arrow G and then enters two ducts 24, 24' issuing into two measuring chambers 25, 25', into which are respectively introduced the measuring electrodes 20, 21, which are shown in dotted line form in FIG. 2.

After rising along electrodes 20, 21 according to arrow H (FIG. 2), the liquid to be measured is introduced into an outlet pipe 26 visible in FIG. 6 and, in accordance with arrow E, enters the discharge pipe 19 before being moved towards the drain.

We claim:
1. A system for regulating the concentration of an oxidizing solution which contains disinfecting molecules and which is circulated in a closed circuit manner in a main pipe, by measuring the Redox Potential of said oxidizing solution, comprising
   a. a reservoir for a concentrated solution of disinfecting molecules connected to said main pipe by readjustment pipe means;
   b. means for selectively directing said concentrated solution into said main pipe;
   c. a measuring cell means having electrode means for measuring the Redox Potential and pH of the oxidizing solution;
   d. a regulator responsive to said electrode means to determine a value of the concentration of the disinfecting molecules in response to signals transmitted by the electrode means, to compare said value with a control value and to control operation of the directing means so as to inject into the main pipe an adequate quantity of the concentrated solution to establish the control value in the oxidizing solution, with injection of the concentrated solution being automatically stopped when the control value is reached:

e. a secondary pipe means leading from the main pipe upstream of the readjustment pipe means relative to flow direction of the oxidizing solution, to the measuring cell means to introduce a portion of the oxidizing solution to the measuring cell means;

f. a reservoir means containing an adapting solution containing a reducing agent and a buffer element; and g. means to supply said adapting solution in a given proportion to said portion of the oxidizing solution in order to reduce its redox potential to a level at which it is possible to measure, and inhibit polarization of the electrode means and buffer the pH of said portion of the oxidizing solution.

2. The system according to claim 1, characterized in that the secondary pipe means is connected to a drain.

3. The system according to claim 2, characterized in that it is equipped with safety device means to detect an operating abnormality in circulation of the portion of said oxidizing solution and to trigger an alarm in response thereto.

4. The system according to claim 1, characterized in that it is equipped with safety device means to detect an operating abnormality in circulation of the portion of said oxidizing solution and to trigger an alarm in response thereto.

5. The system according to claim 1, characterized in that said regulator has a high setpoint and a low setpoint, and said regulator is arranged to maintain said oxidizing solution within limits of said setpoints.

6. The system according to claim 1, characterized in that the secondary pipe means has a valve to control flow therethrough from the main pipe.

7. The system according to claim 6, characterized in that said valve is an electro-valve.

8. The system according to claim 1, characterized in that the adapting solution comprises zero to fifty percent by weight of said reducing agent, zero to fifty percent by weight of an alkali compound, and zero to fifty percent by weight of said buffer element.

9. The system according to claim 8, characterized in that said buffer element comprises a salt.

10. The system according to claim 9, characterized in that said salt is selected from a group consisting of an alkali metal salt, ammonium acetate, and combinations thereof.

11. The system according to claim 10, characterized in that said buffer element further comprises water.

12. The system according to claim 8, characterized in that the adapting solution contains between one percent and five percent by weight of ammonia, between ten percent and fifty percent by weight of ammonium acetate, and between five percent to twenty-five percent by weight of sodium sulphite, and between thirty percent to eighty percent by weight of water.

13. The system according to claim 12, characterized in that the adapting solution contains about one-fortieth by weight of ammonia, about one-quarter by weigh tof ammonium acetate, about one-eighth by weight of sodium sulphite, and about three-fifths by weight of water.

14. The system according to claim 8, characterized in that said measuring cell means defines a reaction chamber in which the adapting solution is mixed with said portion of the oxidizing solution, said measuring cell means further defining a measuring chamber in which said electrode means is positioned and into which is supplied the adapting solution and the portion of the oxidizing solution following mixing thereof.

15. The system according to claim 14, characterized in that said electrode means comprising a first electrode system for measuring redox potential, and a second electrode system for measuring pH.

16. The system according to claim 1, characterized in that the reducing agent is an organic reducing agent.

17. The system according to claim 1, characterized in that the reducing agent is selected from a group consisting of alkali metal thiosulphates bisulphites, sulphites, hypophsphites, hydrazine, an organic reducing agent, and combinations thereof.

18. The system according to claim 1, characterized in that:
a. the adapting solution comprises zero to fifty percent by weight of a reducing agent, zero to fifty percent by weight of an alkali compound, and zero to fifty percent by weight of a buffer element;
b. said buffer element comprises a salt; and
c. the reducing agent is an organic reducing agent.

19. The system according to in claim 1, characterized in that:
a. the adapting solution comprises zero to fifty percent by weight of a reducing agent, zero to fifty percent by weight of an alkali compound, and zero to fifty percent by weight of a buffer element;
b. said buffer element comprises a salt; and
c. the reducing agent is selected from a group consisting of alkali metal thiosulphates, bisulphites, sulphites, hypophsphites, hydrazine, and combinations thereof.

20. The system according to claim 1, characterized in that said measuring cell means defines a reaction chamber in which the adapting solution is mixed with said portion of the oxidizing solution, said measuring cell means further defining a measuring chamber in which said electrode means is positioned and into which is supplied the adapting solution and the portion of the oxidizing solution following mixing thereof.

21. The system according to claim 20, characterized in that said electrode means comprising a first electrode system for measuring redox potential, and a second electrode system for measuring pH.

* * * * *

UNITED STATES PATENT AND TRADEMARK OFFICE
CERTIFICATE OF CORRECTION

PATENT NO. : 4,874,498

DATED : October 17, 1989

INVENTOR(S) : Charles Bousser and Jean-Michel Freal-Saison

It is certified that error appears in the above-identified patent and that said Letters Patent is hereby corrected as shown below:

On the title page, under item [19], "Freal-Saison" should be
-- Bousser et al.--.

On the title page, line [75] Inventor should be changed to --
[75] Inventors: Charles Bousser Sarry; Jean Michel Freal-Saison, Chatou, both of France --.

Signed and Sealed this

Eighth Day of December, 1992

Attest:

DOUGLAS B. COMER

Attesting Officer

Acting Commissioner of Patents and Trademarks